United States Patent
Hiejima et al.

(10) Patent No.: US 7,186,223 B2
(45) Date of Patent: Mar. 6, 2007

(54) GUIDE WIRE

(75) Inventors: Katsuhiro Hiejima, Osaka (JP); Shinji Osawa, Osaka (JP)

(73) Assignee: Nipro Corporation, Osaka (JP)

( * ) Notice: Subject to any disclaimer, the term of this patent is extended or adjusted under 35 U.S.C. 154(b) by 434 days.

(21) Appl. No.: 10/115,933

(22) Filed: Apr. 5, 2002

(65) Prior Publication Data

US 2002/0188188 A1  Dec. 12, 2002

(30) Foreign Application Priority Data

Apr. 10, 2001  (JP) ............................. 2001-111118

(51) Int. Cl.
*A61B 5/00* (2006.01)
*A61M 25/00* (2006.01)

(52) U.S. Cl. .................................... 600/585

(58) Field of Classification Search ............. 600/433, 600/434, 435, 585; 604/164.01, 164.13, 604/171
See application file for complete search history.

(56) References Cited

U.S. PATENT DOCUMENTS

| 4,922,924 | A | | 5/1990 | Gambale et al. ............ 128/772 |
| 4,932,419 | A | * | 6/1990 | de Toledo ................... 600/585 |
| 5,174,302 | A | | 12/1992 | Palmer ........................ 128/772 |
| 5,465,732 | A | | 11/1995 | Abele .......................... 128/772 |
| 5,520,194 | A | * | 5/1996 | Miyata et al. .............. 600/585 |
| 5,640,970 | A | | 6/1997 | Arenas ........................ 128/772 |
| 5,647,127 | A | * | 7/1997 | Miyata et al. ............. 29/896.9 |
| 5,951,496 | A | * | 9/1999 | Willi .......................... 600/585 |
| 5,984,877 | A | * | 11/1999 | Fleischhacker, Jr. ........ 600/585 |
| 2001/0037125 | A1 | * | 11/2001 | Mirarchi ..................... 606/190 |
| 2002/0019599 | A1 | * | 2/2002 | Rooney et al. ............. 600/585 |

FOREIGN PATENT DOCUMENTS

| DE | 198 23 414 A1 | 6/1999 |
| EP | 0 666 086 A1 | 8/1995 |
| JP | 09-038210 A | 2/1997 |
| WO | 99/65558 A1 | 12/1999 |

\* cited by examiner

*Primary Examiner*—Max F. Hindenburg
*Assistant Examiner*—Jonathan Foreman
(74) *Attorney, Agent, or Firm*—Kubovcik & Kubovcik

(57) ABSTRACT

A guide wire, which has excellent follow-up characteristics, sufficients contrasting characteristics and flexibility at a distal end portion thereof and high elasticity at a proximal end portion thereof, includes a core wire, and a coil wire provided on the distal end portion of this core wire coaxially therewith. The coil wire is formed by winding a plurality of wires, which are formed of different constituent materials and placed side by side on a plane, uniformly in an axial direction of the core wire so that the wires are adjacent to each other on the same plane.

3 Claims, 3 Drawing Sheets

GUIDE WIRE

BACKGROUND OF THE INVENTION

This invention relates to a guide wire. More particularly, the invention relates to a guide wire of excellent follow-up characteristics having sufficient X-ray contrasting characteristics and flexibility at a distal end portion of the guide wire, and high elasticity at a proximal end portion of the guide wire.

In order to examine and remedy an affected part of the vascular system, a catheter has been introduced into a blood vessel or a vascular cavity other than a blood vessel. A guide wire is used for the introduction of such a catheter into the vascular cavity. For example, in a percutaneous transluminal coronary angioplasty (PTCA), a guide wire is inserted through an expansible catheter provided with a balloon at a distal end of the catheter. This guide wire is made to reach an objective constriction as a objective branch of a coronary artery is selected under a radioscope. The guide wire is further forced into the constriction and passed therethrough. The catheter is thereafter introduced into the constriction along the guide wire so as to position the balloon in the constriction, the constriction being expanded by expanding the balloon.

A guide wire is desired to have torque communicability so that a distal end of the guide wire can face in a desired direction so as to allow the guide wire to reach an objective part. The torque communicability is an ability such that when the guide wire is turned by hand, a resultant turning force is transmitted to a distal end of the guide wire. A guide wire introduction operation is carried out with exposure of the guide wire to an x-ray as a position of a distal end of the guide wire is ascertained, so that the distal end of the guide wire needs to have X-ray contrasting characteristics. In order to further advance the guide wire into a vascular cavity which branches in a complicated manner, the guide wire needs to have a flexibility (follow-up characteristics) which permits the guide wire to be transformed following up a shape of the vascular cavity.

A guide wire including a core wire having a distal end portion and a proximal end portion, and a coil wire provided so as to be wound around the distal end portion of the core wire has been proposed (Publication WO99/65558, Japanese Patent Laid-Open No. 38210/1997, etc.). Each of these guide wires has excellent torque communicability, excellent X-ray contrasting characteristics of the distal end portion of the guide wire and excellent follow-up characteristics.

In the guide wire disclosed in the publication of WO99/65558, one of an inner layer and an outer layer of a coil wire is formed of a radiation impermeable material, and the other layer is formed of a material of high strength. Suitably selecting a ratio of the materials gives a distal end of the guide wire flexibility and excellent X-ray contrasting characteristics. The guide wire disclosed in Japanese Patent Laid-Open No. 38210/1997 uses a coil wire formed by butt welding ends of a radiation impermeable wire rod and a radiation permeable wire rod together, reducing a diameter of the resultant product and drawing out a length thereof to obtain a single extra fine element coil wire, and winding this element coil wire. This guide wire enables itself to be inserted into a micro blood vessel owing to a smooth and uniform bent shape of the guide wire.

Each of these related art guide wires is formed by combining a wire rod of a material having high contrasting characteristics and a wire rod of a material of high elasticity with each other by a method including welding and the like so as to give the final coil wire properties of both excellent contrasting characteristics and high elasticity, reducing a diameter of the resultant wire rod and drawing out a length thereof to obtain a single wire, and winding this wire. Therefore, it has been difficult to gradually increase the elasticity of the coil wire toward the proximal end thereof.

SUMMARY OF THE INVENTION

The present invention has been made in view of the above-mentioned circumstances, and provides a guide wire of excellent follow-up characteristics, a distal end portion of which has sufficient contrasting characteristics and flexibility, and a proximal end of which has high elasticity.

In order to solve the above-mentioned problems, the inventors of the present invention formed a coil by placing a plurality of wires formed of different constituent materials side by side on a plane so that the wires were adjacent to each other on the same plane, and winding these wires uniformly in the axial direction of the core wire. As a result, it has been found that the above-mentioned problems could be solved, and the present invention was completed.

Namely, the present invention relates to a guide wire with radiation impermeability and flexibility provided to a distal end portion of the guide wire, comprising a core wire which has a distal end portion and a proximal end portion, and which decreases in diameter of a circular cross-section of the core wire toward the distal end portion of the core wire, and a coil wire of a constant diameter provided on the distal end portion of the core wire and provided coaxially with the core wire, the coil wire being formed by placing a plurality of wires of different constituent materials side by side on a plane so that the wires are adjacent to each other on the same plane, and winding the wires uniformly in an axial direction of the core wire.

The coil wire preferably employed in the present invention may be a coil wire having a first wire, a distal end portion of which is formed of a radiation impermeable material and the other portion of which is formed of a radiation permeable and highly elastic material, and a second wire, a whole of which is formed of a radiation permeable and highly elastic material; a coil wire having a first wire, a distal end portion of which is formed of a radiation impermeable material and the other portion of which is formed of a radiation permeable and highly elastic material, and a second wire, a whole of which is formed of a radiation impermeable and highly elastic material; or a coil wire having a first wire and a second wire, a distal end portion of each of which is formed of a radiation impermeable material and the other portion of each of which is formed of a radiation permeable and highly elastic material with the distal end portion of the second wire being longer than that of the first wire.

The radiation impermeable and highly elastic material of the second wire is preferably a metal selected from the group including tungsten, tantalum, an alloy containing tungsten as a main component and an alloy containing tantalum as a main component. The radiation impermeable material of the second wire is preferably at least one metal selected from the group including platinum, gold, iridium, tungsten and tantalum. The radiation impermeable material of the first wire is preferably at least one metal selected from the group including platinum, gold and iridium. The radiation permeable and highly elastic material is preferably one metal selected from the group including stainless steel, piano wire and an amorphous alloy.

DESCRIPTION OF THE DRAWINGS

Referring to the preferred embodiments and attached drawings, an embodiment of a guide wire of the present invention will hereinafter be described. However, the present invention is not limited thereto.

DETAILED DESCRIPTION OF THE INVENTION

Figure 1:
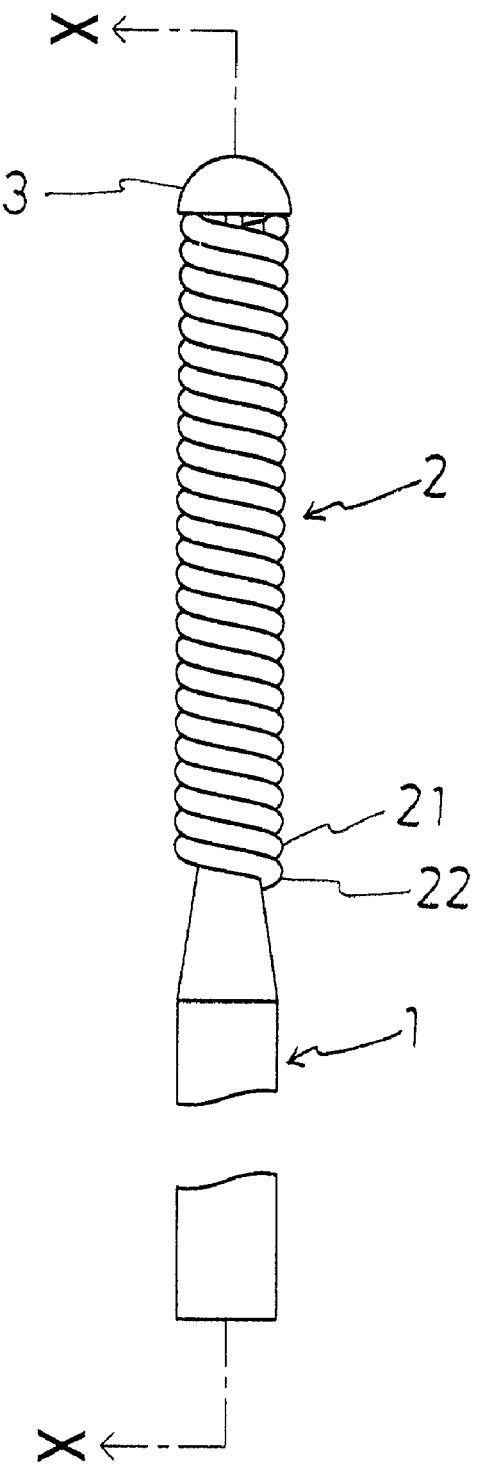
FIG. 1 is a plan view showing an embodiment of a guide wire according to the present invention.
Figure 2:
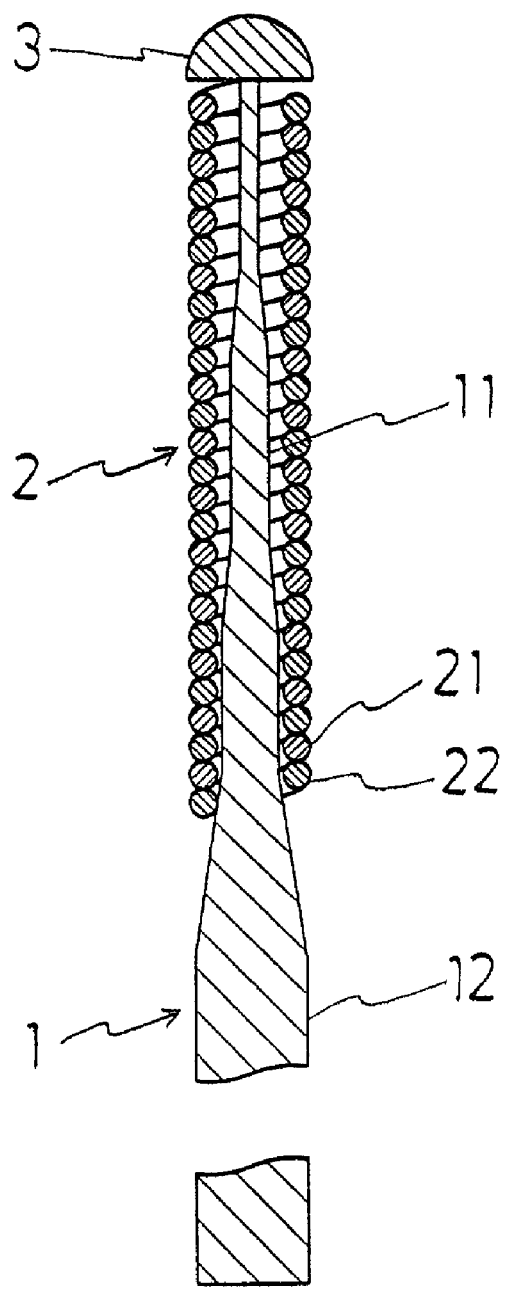
FIG. 2 is a sectional view taken along the line X—X in FIG. 1.

A guide wire according to the present invention includes a core wire 1, and a coil wire 2 provided coaxially with the core wire 1 and on a distal end portion of the core wire 1. The coil wire 2 is formed by winding uniformly in the axial direction a plurality of wires of different constituent materials which are previously placed side by side on a plane so that the wires are adjacent to each other on the same plane. Radiation impermeable characteristics and flexibility are given to the distal end portion of each of the wires. FIG. 1 and FIG. 2 show a guide wire in which the coil wire 2 includes a first wire 21 and a second wire 22.

The core wire 1 has a distal end portion 11 and a proximal end portion 12, and a circular cross-section decreasing in diameter at the distal end portion 11 toward the distal end of the core wire 1. The diameter of the distal end portion of the core wire 1 is preferably 0.10 mm to 0.15 mm and the diameter of the proximal end portion thereof is preferably 0.25 mm to 0.35 mm. The core wire 1 is formed of a general radiation permeable and highly elastic material, which permits radiation, such as X-rays, to pass therethrough, for example, stainless steel or an amorphous alloy. The coil wire 2 having a constant diameter is wound around this core wire 1 coaxially at the distal end portion of the core wire 1.

The coil wire 2 is formed by winding uniformly in the axial direction (for example, around an axis of a core tube) a plurality of wires (in FIG. 1, the first wire 21 and second wire 22) of different constituent materials placed side by side on a plane so that the wires are adjacent to each other on the same plane. The diameter of each of the plurality of wires is preferably at most 0.06 mm and the diameter of the coil wire is preferably at most 0.35 mm. In the coil wire 2 thus formed, the first wire 21 and the second wire 22 are wound alternately as is understood from FIG. 2. The core wire 1 is inserted into a lumen of the coil wire 2 previously wound to form the guide wire.

Figure 3:
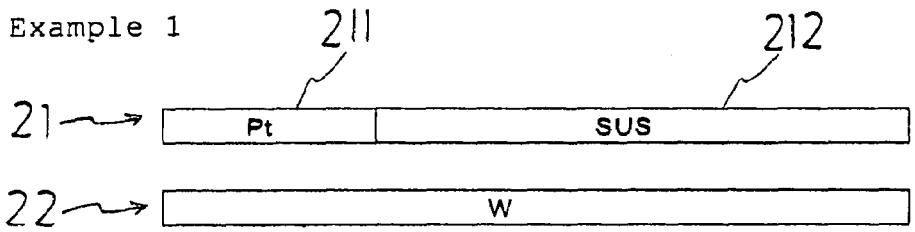
FIG. 3 is a drawing showing a plurality of embodiments of a coil wire in the present invention.
Figure 3:
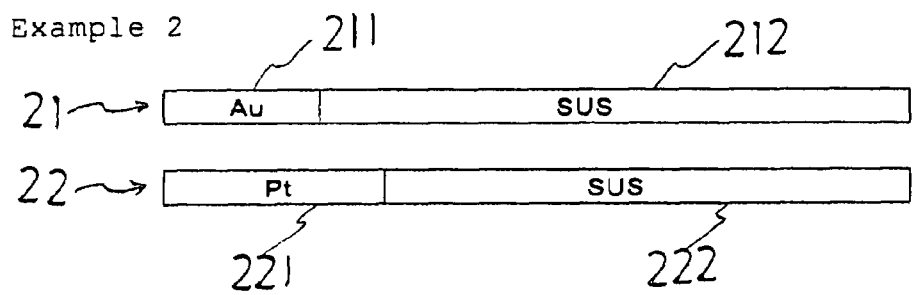
Figure 3:
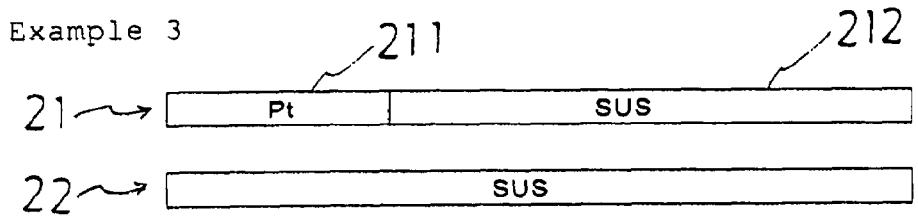
Figure 3:
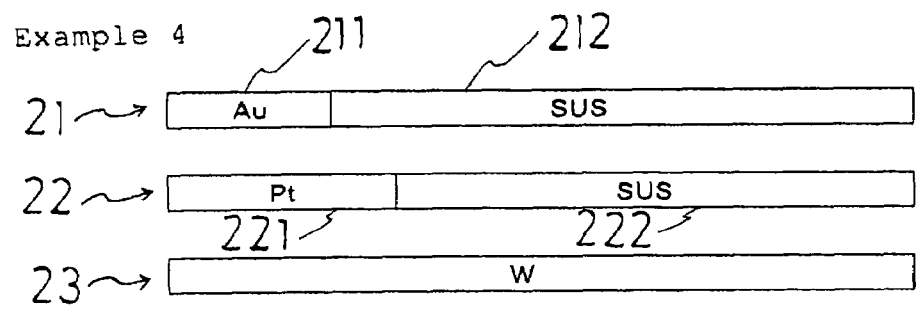

As shown in FIG. 3, a distal end portion 211 of the first wire 21 is formed of a radiation impermeable material, and the other portion 212 of the first wire 21 is formed of a radiation permeable and highly elastic material. The second wire 22 may be wholly formed of either a radiation permeable and highly elastic material or a radiation impermeable and highly elastic material. A distal end portion 221 of the second wire 22 may also be formed of a radiation impermeable material, and the other portion 222 of the second wire 22 may be formed of a radiation permeable and highly elastic material with the distal end portion 221 longer than the distal end portion 211 of the first wire 21. When both of the distal end portion 211 of the first wire 21 and the distal end portion 221 of the second wire 22 are formed of a radiation impermeable material and both of the other portions 212 and 222 are formed of a radiation permeable and highly elastic material, a third wire 23 as shown in Example 4 of FIG. 3, a whole of which is formed of a radiation permeable and highly elastic material, may be added as a wire forming the coil wire 2. The third wire 23 may also be a wire (not shown) in which the distal end portion of the third wire 23 is formed of a radiation impermeable material, and the other portion of the third wire 23 is formed of a radiation permeable and highly elastic material and in which the distal end portion is longer than a distal end portion 221 of a second wire 22. The portion formed of the radiation impermeable material preferably occupies about 10% of each wire in terms of length from the distal end in each wire.

EXAMPLES OF THE INVENTION

The present invention will be explained further with reference to Examples. The Examples, however, should not be construed as limiting the scope of the invention but as merely providing illustrations of certain of the presently preferred embodiments of the invention.

Example 1

As shown in Example 1 of FIG. 3, a first wire, a distal end portion of which is formed of platinum (Pt) as a radiation impermeable material and a proximal end portion of which is formed of stainless steel (SUS) as a radiation permeable and highly elastic material and a diameter of which is about 0.06 mm, and a second wire, a whole of which is formed of tungsten (W) as a radiation impermeable and highly elastic material and a diameter of which is about 0.06 mm, were placed side by side on a plane so that the wires are adjacent to each other on the same plane and were uniformly wound around an axis of a core tube to form a coil wire a diameter of which is about 0.35 mm. The coil wire of Example 1 had a distal end portion formed of platinum (Pt) and tungsten (w), and a proximal end portion formed of stainless steel (SUS) and tungsten (W).

Example 2

As shown in Example 2 of FIG. 3, a first wire, a distal end portion of which is formed of gold (Au) as a radiation impermeable material and the other portion of which is formed of stainless steel (SUS) as a radiation permeable and highly elastic material and a diameter of which is about 0.06 mm, and a second wire, a distal end portion of which is formed of platinum (Pt) as a radiation impermeable material and the other portion of which is formed of stainless steel (SUS) as a radiation permeable and highly elastic material and a diameter of which is about 0.06 mm, were placed side by side on a plane so that the wires are adjacent to each other on the same plane and uniformly wound around an axis of a core tube to form a coil wire a diameter of which is about 0.35 mm. The coil wire of Example 2 had a distal end portion formed of gold (Au) and platinum (Pt), an intermediate portion formed of stainless steel (SUS) and platinum (Pt), and a proximal end portion formed of stainless steel (SUS).

Example 3

As shown in Example 3 of FIG. 3, a first wire, a distal end portion of which is formed of platinum (Pt) as a radiation impermeable material and the other portion of which is formed of stainless steel (SUS) as a radiation permeable and highly elastic material and a diameter of which is about 0.06 mm, and a second wire, a whole of which is formed of stainless steel (SUS) as a radiation impermeable and highly elastic material and a diameter of which is about 0.06 mm, were placed side by side on a plane so that the wires are adjacent to each other on the same plane and uniformly wound around an axis of a core tube to form a coil wire a diameter of which is about 0.35 mm. The coil wire of Example 3 had a distal end portion formed of platinum (Pt) and stainless steel (SUS), and a proximal end portion formed of stainless steel (SUS)

Example 4

As shown in Example 4 of FIG. 3, a first wire, a distal end portion of which is formed of gold (Au) as a radiation impermeable material and the other portion of which is formed of stainless steal (SUS) as a radiation permeable and highly elastic material and a diameter of which is about 0.06 mm, a second wire, a distal end portion of which is formed of platinum (Pt) as a radiation impermeable material and the other portion of which is formed of stainless steal (SUS) as a radiation permeable and highly elastic material and a diameter of which is about 0.06 mm, and a third wire, a whole of which is formed of tungsten (W) as a radiation impermeable and highly elastic material and a diameter of which is about 0.06 mm, were placed side by side on a plane so that the wires are adjacent to each other on the same plane and uniformly wound around an axis of a core tube to form a coil wire a diameter of which is about 0.35 mm. The coil wire of Example 4 had a distal end portion formed of gold (Au), platinum (Pt) and tungsten (W), an intermediate portion formed of stainless steel (SUS), platinum (Pt) and tungsten (W), and a proximal end portion formed of stainless steel (SUS) and tungsten (W).

Test Method

Five sets of coil wires of each example were prepared. The rigidities of the distal end portion, an intermediate portion (only in Example 2 and 4) and the proximal end portion of each of the five coil wires were measured in accordance with the ISO 9626 standards. Each rigidity shown in Table 1 is an average of the rigidities obtained from the five coil wires. Further, with regard to the contrasting characteristics of the distal end portion of the coil wire in each example, the results shown in Table 1 were obtained.

EFFECT OF THE INVENTION

As is clear from what has been described above, a coil wire having a constant diameter is manufactured in a guide wire of the present invention by winding a plurality of wires uniformly around an axis. As a result, a guide wire of excellent follow-up characteristics, a distal end portion of which has sufficient contrasting characteristics and flexibility and a proximal end portion of which has a high elasticity, can be provided at a low cost by suitably selecting the plurality of wires and thereby regulating the contrasting characteristics, flexibility and high elasticity of the guide wire.

What is claimed is:

1. A guide wire having a distal end portion provided with radiation impermeability and flexibility, comprising a core wire having a distal end portion and a proximal end portion and a circular cross-section decreasing in diameter at the distal end portion toward a distal end of the core wire, and a coil wire having a constant diameter provided coaxially with the core wire and provided on the distal end portion of the core wire, wherein the coil wire consists of two wires which are adjacent to each other in an axial direction of the core wire and which are alternately wound around the core wire uniformly in an axial direction of the core wire, and wherein a distal end portion of one of said two wires is formed of a radiation impermeable material selected from the group consisting of platinum, gold and iridium and a remaining portion of which is formed of a radiation permeable and elastic material selected from the group consisting of stainless steel, piano wire and an amorphous alloy, and a whole of the other of said two wires is formed of a radiation permeable and elastic material selected from the group consisting of stainless steel, piano wire and an amorphous alloy or a radiation impermeable and elastic material selected from the group consisting of tungsten, tantalum, an alloy containing tungsten as a main component, and an alloy containing tantalum as a main component.

2. A guide wire having a distal end portion provided with radiation impermeability and flexibility, comprising a core wire having a distal end portion and a proximal end portion and a circular cross-section decreasing in diameter at the

TABLE 1

| | Rigidity (mm)/Component | | | contrasting |
| | Distal end portion | Intermediate portion | Proximal end portion | character- istics |
| --- | --- | --- | --- | --- |
| Example 1 | 1.38/Pt + W | — | 1.61/SUS + W | ○○*1 |
| Example 2 | 0.62/Au + Pt | 1.15/Pt + SUS | 1.23/SUS | ○○ |
| Example 3 | 1.15/Pt + SUS | — | 1.23/SUS | ○*2 |
| Example 4 | 1.07/Au + Pt + W | 1.37/SUS + Pt + W | 1.46/SUS + W | ○○ |

*1○○: Very good *2○: Good

The more the rigidity of the coil wire increases, the more the elasticity thereof increases. It can be understood from Table 1 that the elasticity of the coil wire in each example increases gradually toward the proximal end portion, and that the proximal end portion has high elasticity. It can also be understood that the contrasting characteristics of the distal end portions of the coil wire in each example were very good.

distal end portion toward a distal end of the core wire, and a coil wire having a constant diameter provided coaxially with the core wire and provided on the distal end portion of the core wire, wherein the coil wire consists of two wires which are adjacent to each other in an axial direction of the core wire and which are alternately wound around the core wire uniformly in an axial direction of the core wire, and wherein a distal end portion of each of said two wires is formed of a radiation impermeable material selected from the group consisting of platinum, gold and iridium and a remaining portion of each of which is formed of a radiation permeable and elastic material selected from the group consisting of stainless steel, piano wire arid an amorphous alloy, the distal end portion formed of a radiation impermeable material of one of said two wires being longer than that of the other wire.

3. A guide wire having a distal end portion provided with radiation impermeability and flexibility, comprising a core wire having a distal end portion and a proximal end portion and a circular cross-section decreasing in diameter at the distal end portion toward a distal end of the core wire, and a coil wire having a constant diameter provided coaxially with the core wire and provided on the distal end portion of the core wire, wherein the coil wire consists of three wires which are adjacent to each other in an axial direction of the core wire and which are alternately wound around the core wire uniformly in an axial direction of the core wire, and wherein a distal end portion of two of said three wires is formed of a radiation impermeable material selected from the group consisting of platinum, gold and iridium and a remaining portion is formed of a radiation permeable and elastic material selected from the group consisting of stainless steel, piano wire and an amorphous alloy, the distal end portion formed of a radiation impermeable material of one of said two wires being longer than that of the other of said two wires and a whole of the third of said three wires is formed of a radiation impermeable and elastic material selected from the group consisting of tungsten, tantalum, an alloy containing tungsten as a main component, and an alloy containing tantalum as a main component.

* * * * *